(12) United States Patent
Koren et al.

(10) Patent No.: US 7,611,282 B2
(45) Date of Patent: *Nov. 3, 2009

(54) MOBILE COMPUTED RADIOGRAPHY AND DIGITAL RADIOGRAPHY

(75) Inventors: Jacob Koren, Carmelia (IL); Friedrich Ueffinger, Rochester, NY (US); Richard P. Triassi, Rochester, NY (US); Robert Asento, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/207,517

(22) Filed: Sep. 10, 2008

(65) Prior Publication Data

US 2009/0034688 A1 Feb. 5, 2009

Related U.S. Application Data

(63) Continuation-in-part of application No. 11/562,123, filed on Nov. 21, 2006, now Pat. No. 7,438,470, which is a continuation-in-part of application No. 10/997,751, filed on Nov. 24, 2004, now Pat. No. 7,434,997.

(60) Provisional application No. 60/525,316, filed on Nov. 26, 2003.

(51) Int. Cl.
*H05G 1/02* (2006.01)

(52) U.S. Cl. ...................................... 378/198

(58) Field of Classification Search ......... 378/193–198, 378/204; 250/370.08, 370.09, 580–591
See application file for complete search history.

(56) References Cited

U.S. PATENT DOCUMENTS

| | | | |
|---|---|---|---|
| 2,369,454 A | 2/1945 | Goldfield et al. | |
| 4,906,847 A | 3/1990 | Nakajima et al. | |
| 5,270,530 A | 12/1993 | Godlewski et al. | |
| 5,712,482 A | 1/1998 | Gaiser et al. | |
| 5,835,558 A | 11/1998 | Maschke | |
| 6,126,314 A | 10/2000 | Morasse | |
| 6,315,308 B1 | 11/2001 | Konopka | |
| 6,624,438 B2 | 9/2003 | Koren | |
| 6,629,927 B1 | 10/2003 | Mesaros et al. | |
| 7,030,404 B2 | 4/2006 | Berger et al. | |
| 7,438,470 B2 * | 10/2008 | Koren | 378/198 |
| 2004/0028174 A1 | 2/2004 | Koren | |
| 2004/0031939 A1 | 2/2004 | Berger et al. | |
| 2004/0068185 A1 | 4/2004 | Marshall et al. | |
| 2004/0146142 A1 | 7/2004 | Maijala | |
| 2006/0034427 A1 | 2/2006 | Brooks | |
| 2007/0133753 A1 | 6/2007 | Jakob et al. | |

FOREIGN PATENT DOCUMENTS

| | | |
|---|---|---|
| JP | 59-084637 | 5/1984 |
| JP | 2003-248276 | 9/2003 |

* cited by examiner

*Primary Examiner*—Courtney Thomas

(57) ABSTRACT

A mobile apparatus. The mobile radiography apparatus includes: a frame; a transport mechanism coupled to the frame, the transport mechanism adapted to facilitate transport of the mobile apparatus between locations; an x-ray source mounted to the frame; a computed radiography (CR) scanner coupled to the frame and adapted to acquire one or more images from an image recording medium; a storage area disposed on the frame configured to removably retain at least one digital radiography (DR) detector; and a display coupled to the frame and connected to the CR scanner and the DR detector to display the one or more images acquired by the CR scanner or DR detector.

6 Claims, 13 Drawing Sheets ary unit of FIG. 5A.

MOBILE COMPUTED RADIOGRAPHY AND DIGITAL RADIOGRAPHY

CROSS REFERENCE TO RELATED APPLICATIONS

This application is a Continuation-in-Part of commonly assigned application U.S. Ser. No. 11/562,123, entitled "MOBILE COMPUTED RADIOGRAPHY", filed on Nov. 21, 2006, now U.S. Pat. No. 7,438,470, in the name of Koren, which is a Continuation-in-Part of commonly assigned application U.S. Ser. No. 10/997,751, entitled "MOBILE COMPUTED RADIOGRAPHY", filed on Nov. 24, 2004, now U.S. Pat. No. 7,434,997 in the name of Koren, which claims the benefit of U.S. Provisional Application 60/525,316 filed Nov. 26, 2003, entitled "MOBILE COMPUTED RADIOGRAPHY," by Koren, all of which are incorporated herein in their entirety.

FIELD OF THE INVENTION

The invention relates generally to the field of medical imaging, and in particular to computed radiography (CR) and digital radiography (DR).

BACKGROUND OF THE INVENTION

Modern medical facilities such as hospitals or emergency care facilities are often large and complex organizations. A medical facility may be organized into various branches or wings that specialize in a particular type of patient care and/or expertise. For example, a medical facility may have a radiology and/or radiography department that handles various medical imaging tasks such as X-ray and MRI for the medical facility. Patients requiring an X-ray, for example, must be transported to the radiology center or department.

Conventional radiography centers (e.g., as found in radiology departments in medical facilities) may include multiple radiography rooms each equipped with X-ray systems for exposing patients and image recording media (e.g., films, phosphor plates, and the like) to radiation, so as to acquire X-ray images of the patients for diagnosis, treatment, and the like. Often, an exposed image recording medium is loaded into a holder or cassette for transporting the exposed medium from the room with the X-ray exposure system to a central processing center. For example, a cassette holding exposed film typically is hand-carried from the exposure area to a central chemical processing station associated with a main darkroom for developing the exposed film.

A cassette holding an exposed storage phosphor plate typically is hand-carried from the exposure area to, for example, a mainframe CR scanner, which scans the phosphor plate to acquire the image stored thereon. Exemplary CR scanners are described in U.S. Pat. No. 6,624,438 entitled "SCANNING APPARATUS," by Koren, which is herein incorporated by reference in its entirety.

This general concept of workflow (i.e., radiation exposure in radiography rooms, and central processing elsewhere) typically dictates the architectural design of the X-ray room layout of a conventional radiography processing center (e.g., in a medical facility). In particular, in a typical layout, a patient corridor may be located in front of a row of X-ray exposure rooms, and a staff corridor may be located behind the row of X-ray exposure rooms, thereby enabling separate traffic flows of patients being imaged and technicians carrying the X-ray cassettes to a central processing area (e.g., main darkroom or a room having a CR scanner).

However, this workflow and organization model results in generally unnecessary traffic, inefficiency and requires significant coordination and organization as described in U.S. application Ser. No. 10/447,733 entitled "DISTRIBUTED AND REDUNDANT COMPUTED RADIOGRAPHY SYSTEMS AND METHODS," by Koren ('733), which is herein incorporated by reference in its entirety. The '733 application describes methods and apparatus for providing distributed and redundant CR systems to avoid "bottlenecks" and other inefficiencies in the central processing workflow architectures.

SUMMARY OF THE INVENTION

A mobile computed radiography (CR) and digital radiography (DR) apparatus. The mobile radiography apparatus includes: a frame; a transport mechanism coupled to the frame, the transport mechanism adapted to facilitate transport of the mobile apparatus between locations; an x-ray source mounted to the frame; a computed radiography (CR) scanner coupled to the frame and adapted to acquire one or more images from an image recording medium; a storage area disposed on the frame configured to removably retain at least one digital radiography (DR) detector; and a display coupled to the frame and connected to the CR scanner and the DR detector to display the one or more images acquired by the CR scanner or DR detector.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
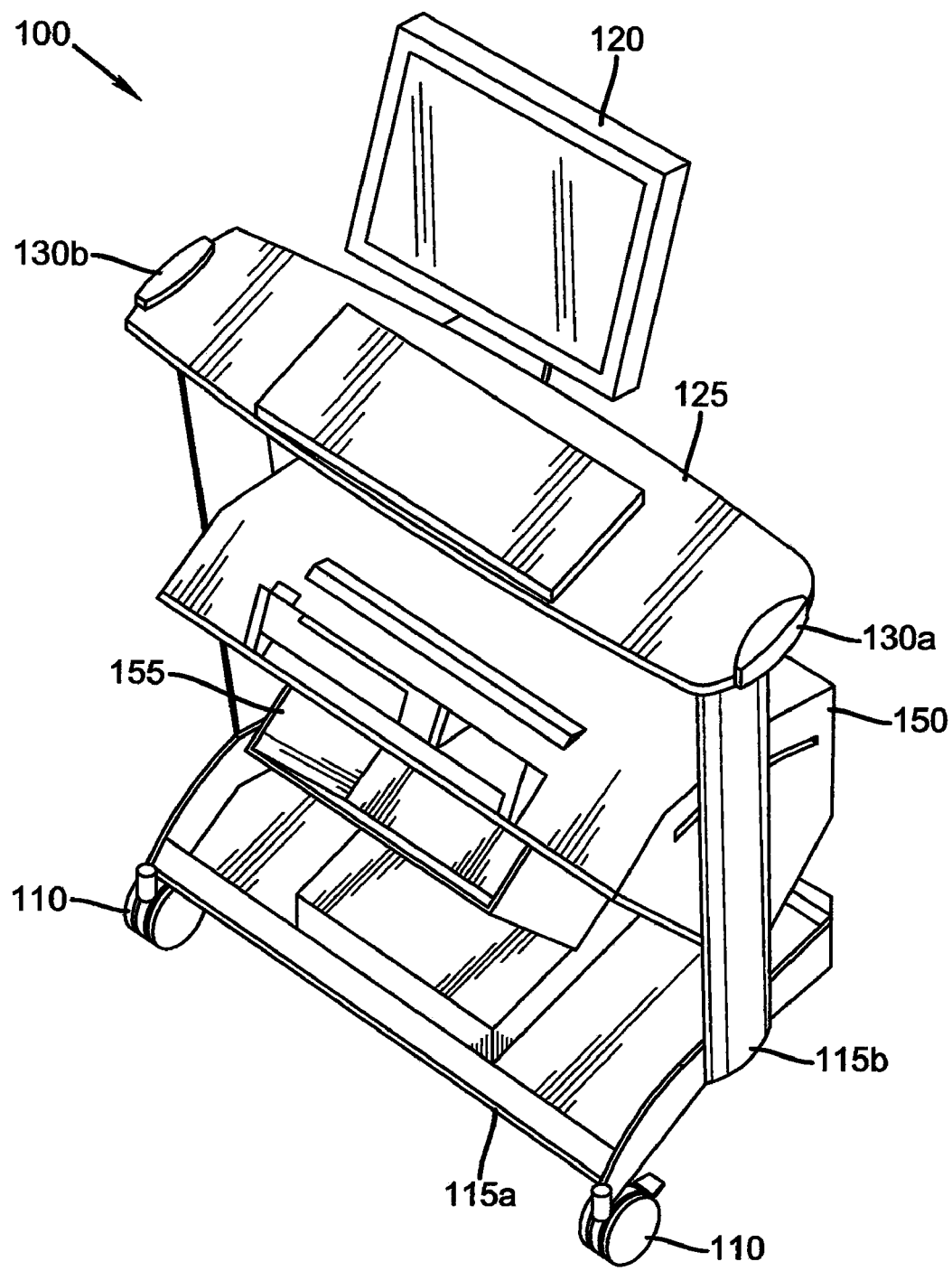
FIG. 1 shows a perspective view of a mobile computed radiography unit in accordance with the present invention.

Imaging equipment such as X-ray devices are often large, expensive and relatively immobile. Accordingly, conventional medical facilities include imaging equipment arranged in a generally permanent location, thus requiring a patient to be brought to the equipment. Such a requirement may result in undo hardship in circumstances when it is difficult or impossible to transport a patient to a designated imaging location.

In particular, patients requiring some form of imaging may be generally immobilized for one reason or another. For example, patients in an intensive care unit (ICU) may be unconscious and connected to various life support equipment required to keep them alive. Elderly patients may not be easily transported and may be vulnerable to injury during attempts to move them. Accordingly, it is often unreasonable, dangerous or sometimes impossible to transport a patient to locations having the imaging equipment necessary to diagnose, treat or otherwise image a patient. While X-ray exposure equipment has been made mobile to permit generally immobile patients to be exposed, CR image acquisition equipment such as CR scanners or readers have not conventionally been equipped to be brought to the patient and/or X-ray exposure equipment.

In addition, as discussed above, many medical facilities are arranged with radiology or radiography departments built to accommodate the central processing model. Some imaging tasks are rather complex and require multiple exposures, precise positioning of the patient and/or techniques involving multiple imaging modalities. In conventional systems, a patient and phosphor plate may be exposed to radiation in an exposure area and the phosphor plate hand-carried to the nearest CR scanner which may be in another room, another department or another building. The phosphor plate must then be scanned to acquire the image and the radiologist or operator must then observe the image to ensure that the patient was properly placed, or to plan additional exposures in multiple exposure diagnostic treatments.

If the obtained image is not acceptable for some reason (e.g., misaligned) the operator, personnel and/or the radiologist must return to the exposure area and adjust the patient or the equipment to correct for the misalignment. In multiple exposure tasks, the patient or equipment must be aligned according to the previous acquired image. The patient must then be exposed again and the procedure repeated. This process requires significant coordination between equipment operators, personnel and radiologists who already may be strained for time, in addition to the additional treatment time for the patient. Arrangements wherein the X-ray exposure equipment and patient and the image acquisition equipment are located remote from one another (e.g., in separate rooms), are therefore generally inconvenient and inefficient.

Applicant has appreciated that smaller, lighter-weight CR scanners, such as those manufactured by OREX™ Computed Radiography, Inc. (OREX) facilitate implementation of more convenient workflow and imaging models. In particular, Applicant has identified the benefits of and developed a CR model including a mobile CR unit. Applicant has appreciated that a mobile CR unit facilitates imaging of generally immobile patients and further streamlines X-ray treatment by enabling the image acquisition equipment (e.g., CR scanner and/or display) to be brought proximate the patient and exposure equipment (e.g., an X-ray device). Various embodiments incorporating aspects of the present invention are described in detail below.

FIG. 1 illustrates a mobile CR unit, in accordance with one embodiment of the present invention. Mobile CR unit 100 includes a CR scanner 150 and wheels 110. The term CR scanner or CR reader refers generally to any device or combination of devices capable of acquiring information from an image recording medium such as a phosphor plate and converting the information into electronic form such as a digital image. In particular, CR scanner refers to any number of laser scanning devices configured to apply a laser to a phosphor plate and detect radiation emitted from the phosphor plate or screen in response to the laser. The detected radiation may then be converted into a digital signal to form an image that can be stored digitally, transmitted electronically and/or viewed directly. For example, the scanning apparatus disclosed in the '438 patent incorporated above are examples of CR scanners. Further exemplary CR scanners include the PcCR™ 1417 system manufactured by Orex. It should be appreciated that CR scanner 150 may be any CR scanner in any variety of arrangements and configurations, as the aspects of the invention are not limited to any particular CR scanner.

Wheels 110 are preferably chosen to enable generally simple transport over the surface of the medical facility in which it is located, for example, over a floor, hallway, and the like. It should be appreciated that other mobile means or transport mechanisms may be used in place of wheels, such as rollers, anti-friction pads or slides. In general, a mobile CR unit may comprise any component or device configured to facilitate movement and/or transport of the mobile CR unit (i.e., any mechanism that makes the unit sufficiently mobile).

CR scanner 150 and wheels 110 may be coupled to support 115a and/or 115b such that actuation of the wheels 110 results in movement of CR scanner 150. For example, wheels 110 may be connected to a base support 115a. CR scanner 150 may be coupled to base support 115a via side supports 115b. CR scanner 150 and wheels 110 need not be integrally coupled to the support. Any arrangement wherein the CR scanner can be transported by actuating a transport mechanism is considered contemplated. For example, wheels could be directly coupled to the CR scanner without departing from the scope of the invention. The term "coupled" refers generally to any mechanical or electrical relationship or interaction capability, wherein coupled components can influence one another and/or are arranged to cooperate with one another. Coupling does not require, but may include, direct physical contact.

Mobile CR unit 100 also includes a display 120 for viewing images acquired by CR scanner 150. Display 120 may be any standard computer monitor, flat screen display, touch sensitive device, and the like. Mobile CR unit 100 may also include a support 125 for the display 120 and/or for various other computer peripheral devices that may be added to the unit as described in more detail in connection with FIG. 4 below. Display 120 may be connected to the CR scanner 150 to receive acquired images in a variety of ways, for example, via a SCSI connections or via a wireless connection.

Support 125 includes grips 130a and 130b to allow an operator or personnel to easily apply force to the mobile CR unit to transport the unit to a desired location. For example, grips 130a and 130b may be made of santoprene or other material to facilitate gripping and relatively simple transport. As described in further detail below, a mobile CR unit preferably includes a portion specifically adapted to provide an operator a generally convenient location to manually engage (e.g., by grabbing, clasping or otherwise handling the portion) the mobile CR unit to transport the unit a desired location. Instead of the grips 130, a bar or other conveniently located portion of the frame of the CR unit may be configured and positioned to allow the operator to conveniently apply force to the CR unit. In some embodiments, the bar, grip or other specifically adapted portion is provided approximately at waist, arm or hand level to make transporting the unit in a fully upright position more convenient so that the unit may be easily walked from one location to another.

CR scanner 150 may include a holder 155 to hold image recording cassettes used to protect and transport image recording media such as phosphor plates as described in further detail in connection with FIGS. 2A and 2B below. Mobile CR unit 100 may be constructed of any material. For example, the support structure may be constructed of plastic, aluminum, steel, titanium or any combination thereof. The aspects of the invention are not limited to any choice of construction material, or combination of construction material.

Mobile CR unit 100 is designed as an integrated, freestanding unit. In particular, components of the unit (e.g., CR scanner, display and transport mechanism) are fixedly attached to a generally integrated body or frame that is made mobile and independent from any X-ray exposure equipment. It should be appreciated that mobile CR unit can be easily transported to any of various desired locations. For example, a generally immobile patient requiring one or more imaging procedures may be located in the ICU of a hospital some distance from the radiology department. A mobile X-ray unit may be available that can be transported to the patient or one may be available locally. Accordingly, a mobile CR unit (e.g., mobile CR unit 100) may be transported to the patient or proximate the X-ray exposure equipment such that the immobile patient may be imaged without having to move and possibly injure the patient.

In circumstances where a patient is generally mobile and can be transported to the X-ray exposure equipment, a mobile CR unit can be transported proximate the X-ray exposure equipment, proximate the radiologist or to any convenient location. The ability to position the CR scanner anywhere desired facilitates efficient use of radiologist resources, and provides an effective workflow model. When multiple images and/or precise positioning of equipment is required, mobile CR unit 100 may be wheeled into the same room as the X-ray exposure device. A patient may be exposed and the phosphor plate immediately loaded into the CR scanner of the mobile unit to acquire a digital image for viewing. An operator or radiologist can receive immediate feedback as to whether the patient and/or X-ray exposure equipment was positioned correctly can view the image for diagnostic purposes, or otherwise process the patient and image without the attendant inefficiencies of conventional systems.

Figure 2A:
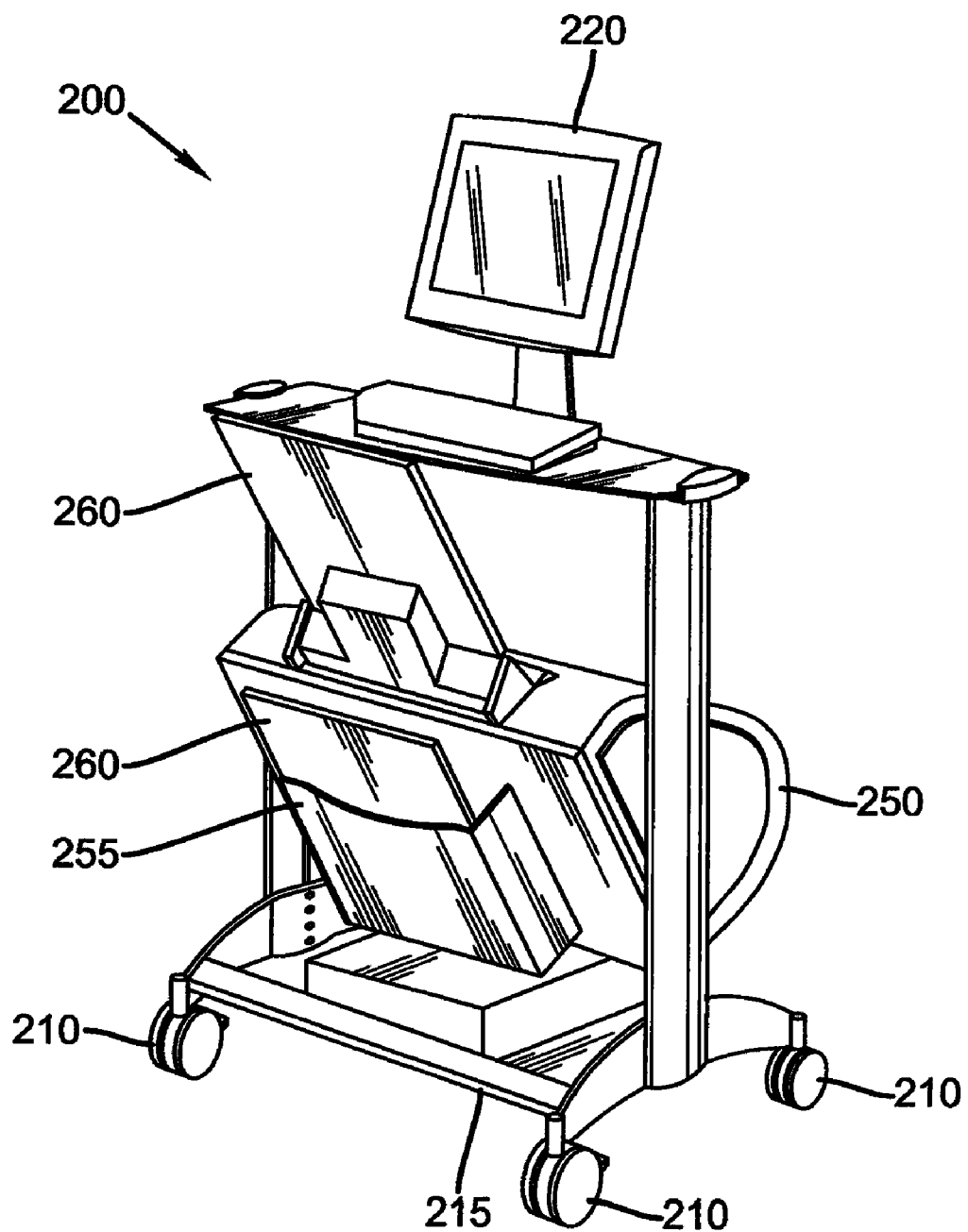
FIGS. 2A and 2B show a perspective view of a mobile computed radiography unit in accordance with the present invention.
Figure 2B:
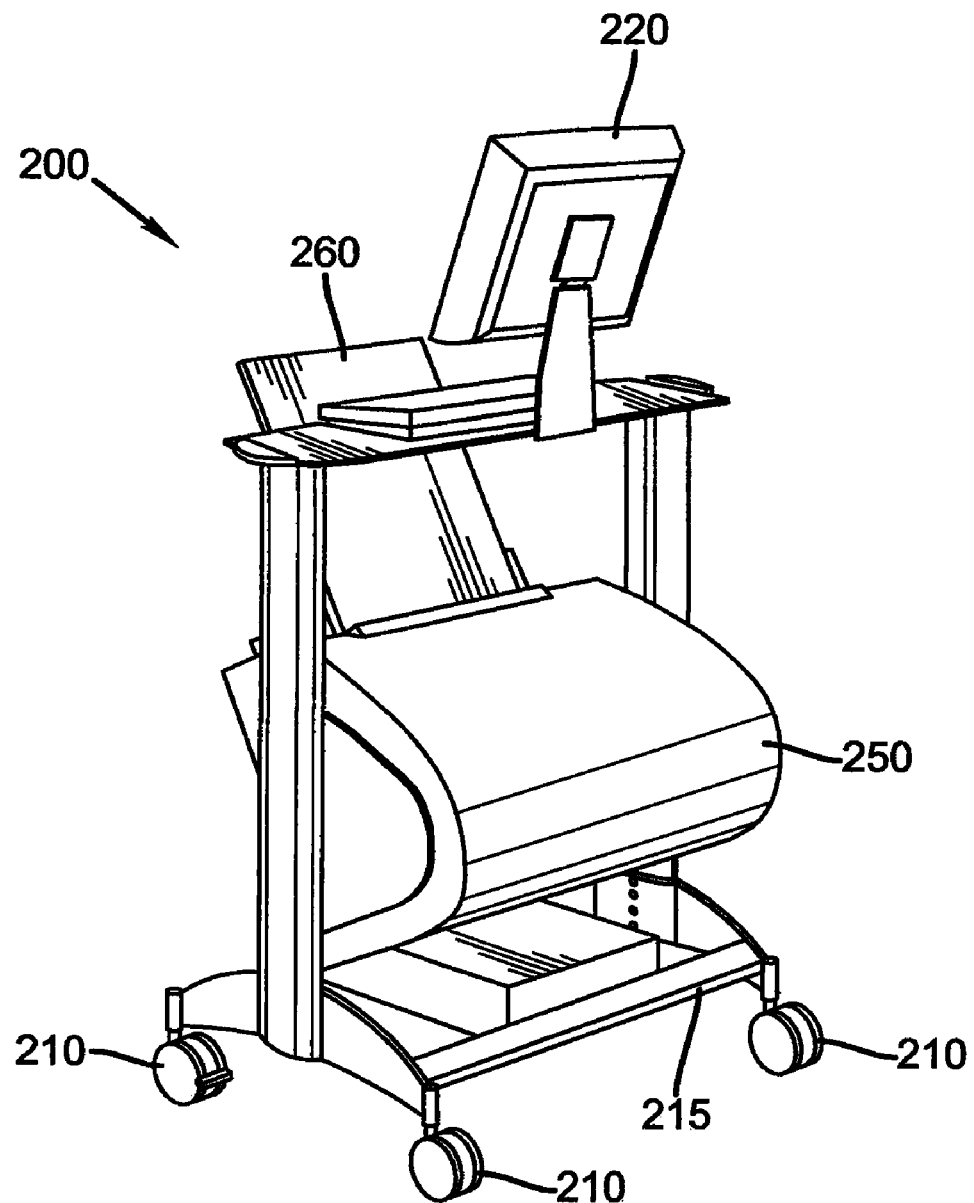

FIGS. 2A and 2B illustrate another embodiment of a mobile CR unit according to aspects of the present invention. Mobile CR unit 200 may be similar to mobile CR unit 100. The unit illustrated in FIG. 2A illustrates cassettes 260 stored in a holder 255. FIGS. 2A and 2B illustrate a cassette inserted into a loader of CR scanner 250 in a position to be scanned. CR scanner 250 may have automatic load features as described in U.S. application Ser. No. 10/431,350 entitled "METHODS AND APPARATUS FOR HANDLING IMAGE RECORDING MEDIA," by Koren which is herein incorporated by reference in its entirety. Mobile CR unit 200 also may have space above support 215 in order to place, for example, a personal computer (PC), other components, or anything else to be transported with the device.

Figure 3A:
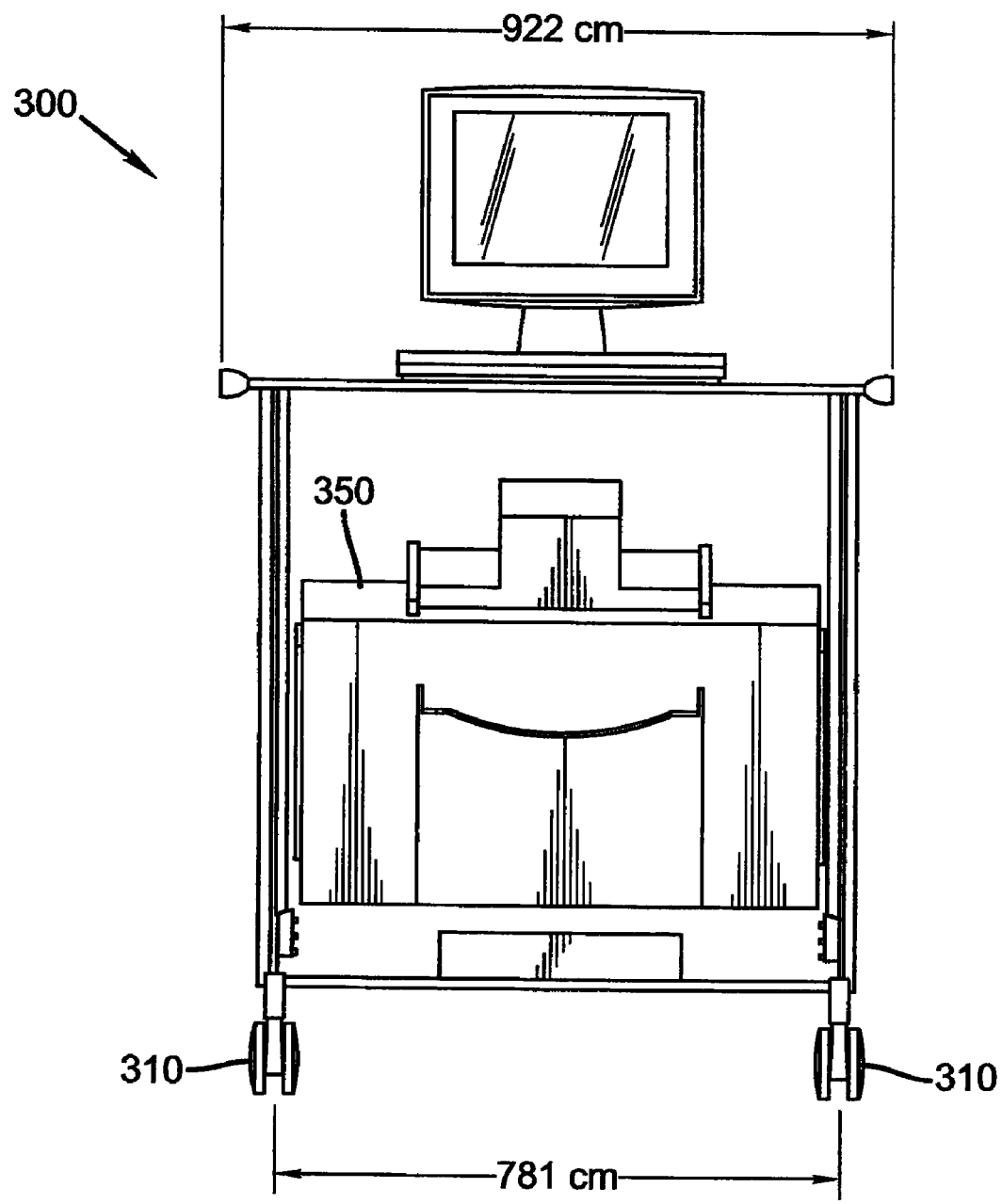
FIG. 3A shows a front view of a mobile computed radiography unit in accordance with the present invention.
Figure 3B:
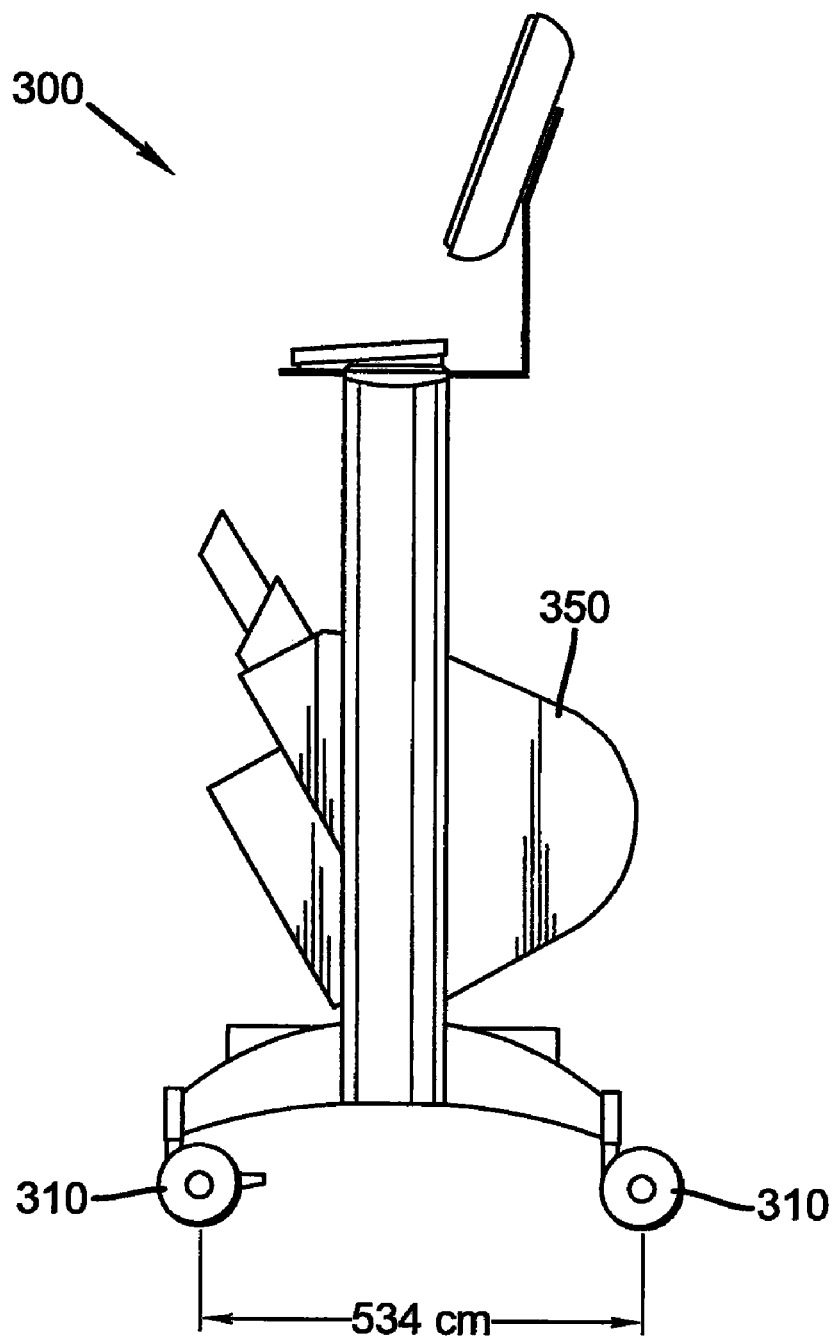
FIG. 3B show a side view of the mobile computed radiography unit of FIG. 3A.
Figure 4:
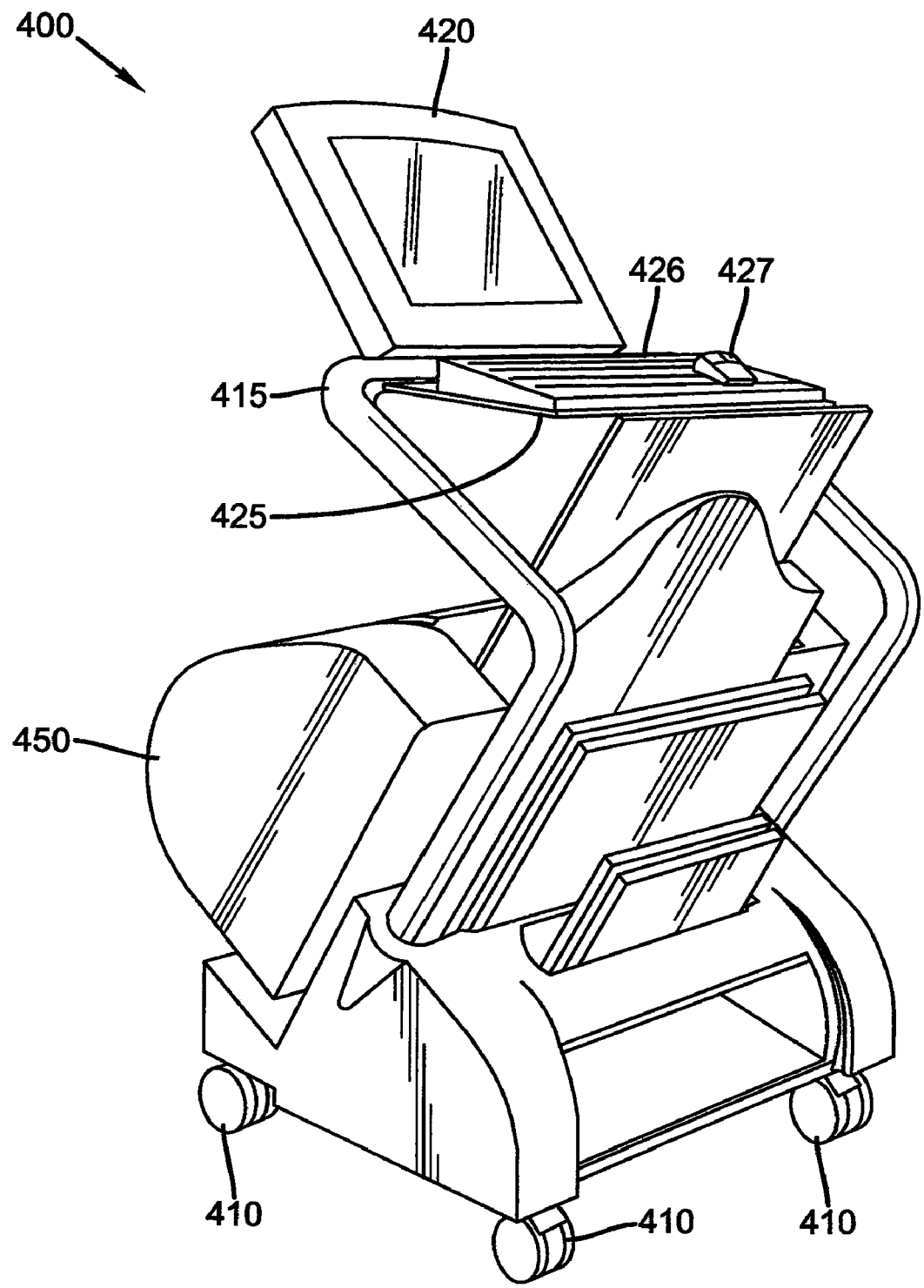
FIG. 4 shows a perspective view of a mobile computed radiography unit in accordance with the present invention.

FIGS. 3A and 3B illustrate another embodiment of a mobile CR unit according to aspects of the present invention. FIG. 3A illustrates a front view and FIG. 3B illustrates a side view of mobile CR unit 300. Exemplary dimensions are labeled on the device to show one embodiment of the size of a mobile CR unit. However, a mobile CR unit can be constructed having any number of different dimensions and sizes and can be constructed to accommodate CR scanners of various sizes. As shown, the FIG. 4 illustrates another embodiment of a mobile CR unit according to the present invention. Mobile CR unit 400 may be similar to the mobile CR unit described in connection with FIGS. 1 through 3B, but having an alternative design. For example, mobile CR unit 400 includes curved supports 415 having display 420 coupled to an upper portion of the supports. In addition, mobile CR unit 400 includes a tray 425 adapted to support a keyboard 426, mouse 427 and perhaps other computer peripheral devices that may be needed to interface with the display 420 and/or acquisition and display software that may be run on a computer system either separate from or incorporated into CR scanner 450.

It should be appreciated that a mobile CR unit may be equipped with standard interfaces. For example, a mobile CR unit may have one or more Universal Serial Bus (USB) ports, parallel ports, serial ports, SCSI ports, and the like. In addition, the mobile CR unit may have a network port such that the unit may be connected to a local area network (LAN), wide area network (WAN), and the like. For example, mobile CR unit may be adapted for connection to the internet to transmit acquired images to remote locations or download images for viewing from other locations.

A network connection may facilitate, for example, remote diagnostics. For example, a technician or operator may transport mobile CR unit 400 to a desired location (e.g., proximate X-ray exposure equipment and/or a generally immobile patient). The technician may expose the patient and immediately acquire an image of the internal structures of the patient. This image may be transmitted over the network to a radiologist who can analyze and/or diagnose the image from a remote location without having to be in the same location as the exposure/acquisition equipment. This may facilitate efficient use of a radiologist's time and may allow expertise to be employed from surrounding or remote areas without having the expertise local to the patient.

In one embodiment, a mobile CR unit includes a wireless, network interface. For example, any of the mobile CR units described herein may include a Wi-Fi interface that allows the mobile CR unit to connect to a Wi-Fi network.

Images, diagnostic and patient information may be transmitted over a LAN, the Internet, and the like, and then stored, processed or analyzed independent of whether the CR unit has a physical connection to a network. Wireless connectivity may increase the general mobility of the unit and may facilitate its integration in the imaging model from virtually anywhere. The type of wireless communication is not limited to Wi-Fi (IEEE 802.11) or any other wireless protocol. For example, infrared protocols such as Infrared Data Association (IrDA) may be used to implement wireless connectivity.

Figure 5C:
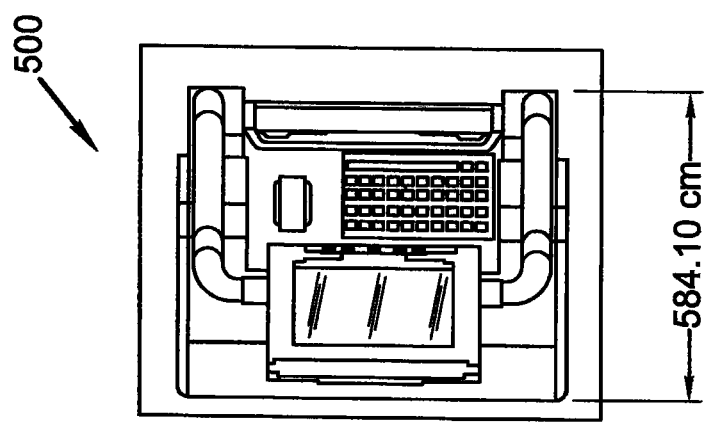
FIG. 5C shows a top view of the mobile computed radiography unit of FIG. 5A.
Figure 5B:
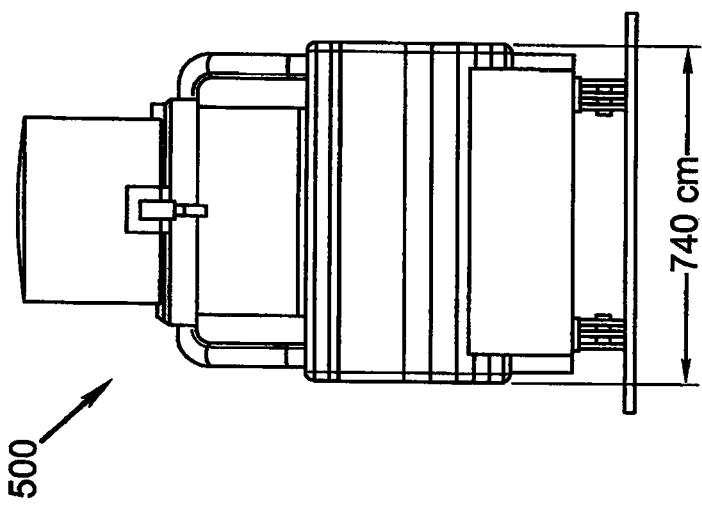
FIG. 5B shows a back view of the mobile computed radiography unit of FIG. 5A.
Figure 5A:
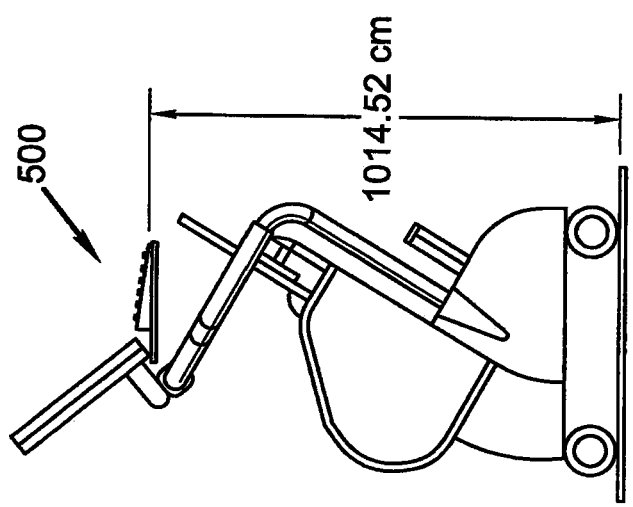
FIG. 5A shows a side view of a mobile computed radiography unit in accordance with the present invention.

FIGS. 5A-5C illustrate another embodiment of a mobile CR unit according to the present invention. FIGS. 5A-5C illustrate some exemplary dimensions for the design illustrated generally in FIG. 4. However, any size and/or dimensions may be used in constructing a mobile CR unit. In addition, any additional components, electronic devices, apparatus for storage, or members to facilitate transport can be added or arranged alone or in combination on a mobile CR unit.

It should be appreciated that the various constructions in the embodiments described in connection with FIGS. 1 through 5C have been ergonomically designed to facilitate relatively simply transport and use. For example, the CR scanner has been positioned relatively low on the device near the transport mechanism such that the device has a low center of gravity. Accordingly, an operator can apply a force to transport mobile CR unit at generally hand/arm level (e.g., by grabbing grips 130*a* and/or 130*b* with the hands and pushing or pulling the unit) without having to worry about tipping over the mobile CR unit and having to bend or reach in order to transport the device.

In addition, the various components of the mobile unit have been arranged having easy access. For example, the display is arranged and can be adjusted for easy viewing and the keyboard may be positioned generally at a height that facilitates natural typing postures for a standing operator. The CR scanner may be disposed with a front facing loader such that cassettes may be simply and easily loaded into and taken out of the CR reader. In addition, the cassette holder may positioned such that plates can be easily and conveniently stored without having to reach or without having to move to the back side of the device. Accordingly, embodiments according to the present invention have been designed to facilitate transport and operation according to natural postures of a human operator and to provide simple access to the CR scanner and peripheral devices such that the mobile unit may be used in crowded or otherwise limited areas. Some embodiments are constructed such that all parts are designed to be fastened to the unit in an integrated fashion to provide a single, specialized mobile unit.

A further embodiment is now described with reference to FIGS. 6 through 9.

Mobile unit 600 includes a CR scanner 605 having an opening 606 into which a cassette is inserted, a display 610, one or more wheels 615, and a frame 620.

Frame 620 includes a handle/grips 625 to which a user can apply force to the mobile unit to transport the mobile unit to a desired location. Handle 625 is preferably at waist, arm, or hand level for convenient transport of the unit in a fully upright position.

Figure 6:
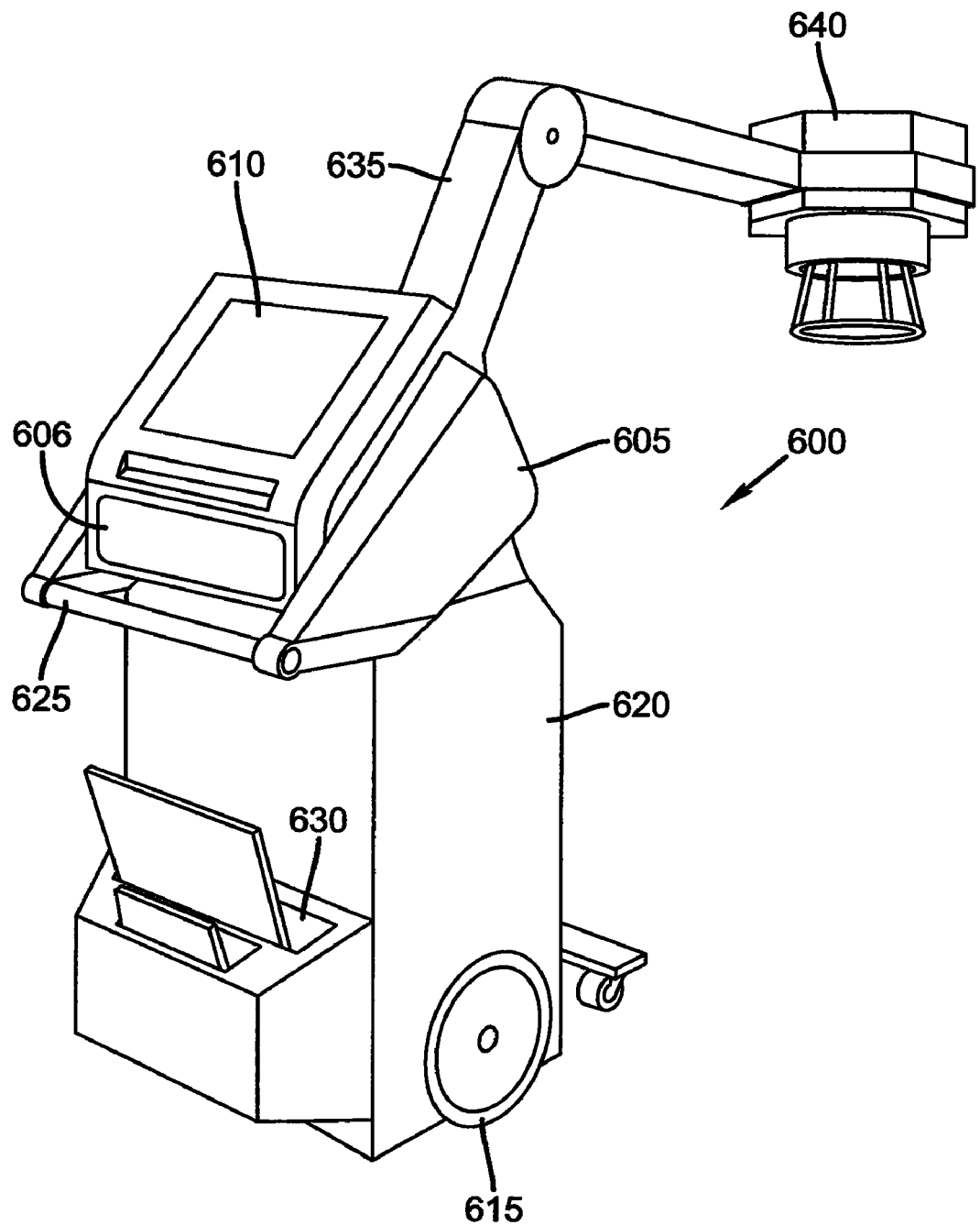
FIG. 6 shows a perspective view of another embodiment of a mobile computed radiography unit in accordance with the present invention.
Figure 7:
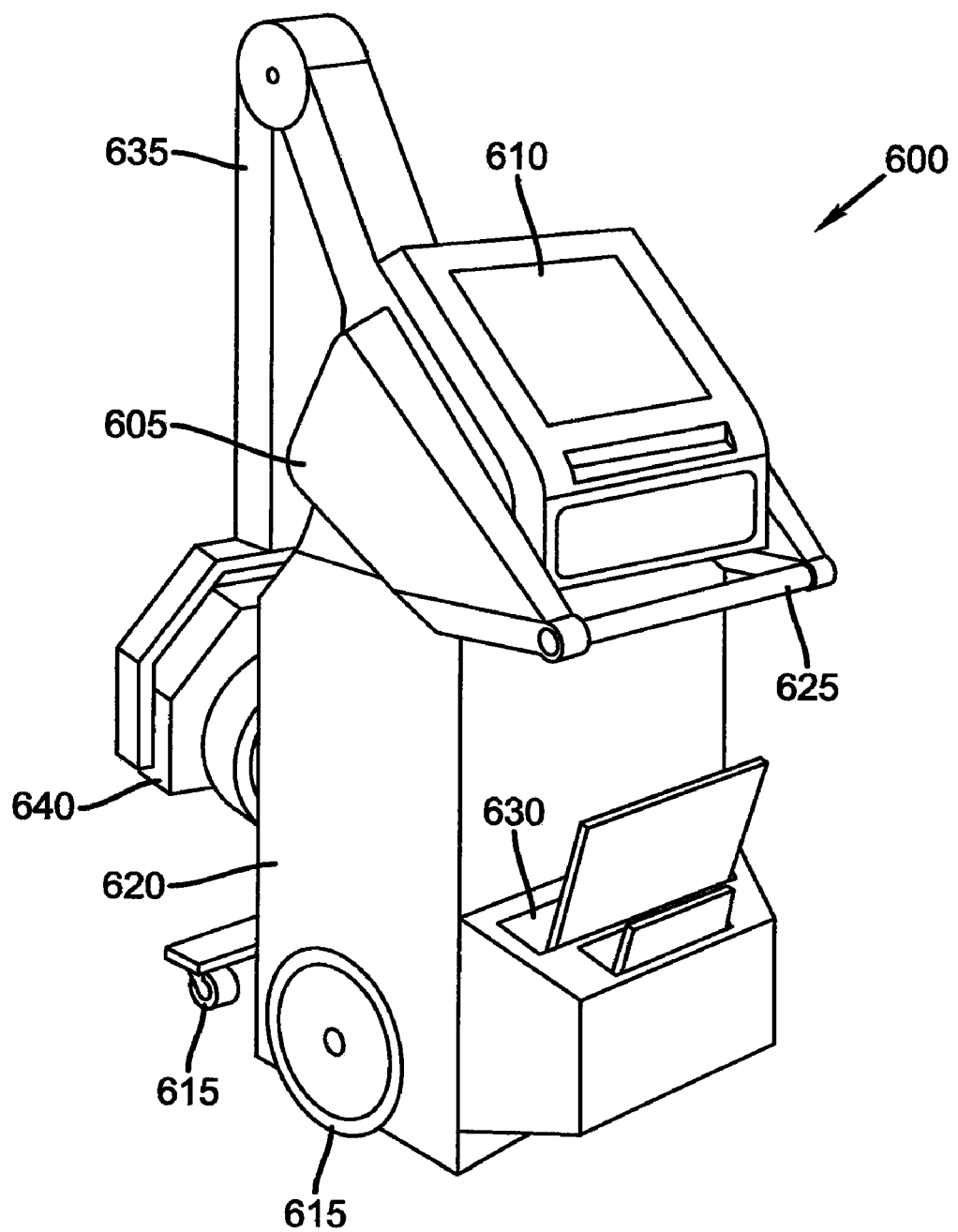
FIG. 7 shows a perspective view of the mobile computed radiography unit of FIG. 6.

Frame 620 further includes holder 630 to hold image recording cassettes used to protect and transport image recording media such as storage phosphor plates. As shown in FIGS. 6 and 7, holder 630 may includes areas of various sizes to hold various size cassettes, since various size cassettes can be scanned by CR scanner 605.

Disposed within frame 620 is a power supply including a battery pack. A power cable can be extended from CR scanner 605 to connect with the power supply. As such, mobile unit 600 is mobile, allowing it to be operated away from a power wall outlet. The battery status can be indicated on display 610 or on another location of mobile unit 600.

Attached to frame 620 is a support member 635 supporting an x-ray source/generator 640. As shown in FIGS. 6 and 7, support member 635 is an arm having an articulated member for supporting x-ray source 640 proximate one end which allows x-ray source 640 to be arranged in a plurality of positions. X-ray source 640 can further be mounted to support member 635 such that is can be rotated about one or more axis. As best shown in FIG. 7, for transport of unit 600, support member 635 and x-ray source 640 can be arranged close to frame 620 for ease of transport. Then, when unit 600 is to be used, support member 635 and x-ray source 640 can be extended from frame 620 for proper positioning, as shown in FIG. 6.

When an image is required, mobile unit 600 can be employed. A cassette, such as a cassette stored in holder 630, is properly positioned relative to the patient. X-ray source 640 is properly positioned for capture of an x-ray image using the cassette. An appropriate energy level and exposure time for the x-ray source is determined, and this information is communicated to mobile unit 600, for example, by means of display 610. A computer processing unit (CPU) of mobile unit 600 can be employed to determine if such information is within generally accepted principles of operation. The exposure information can be shared with the CR scanner, if desired. Exposure by the x-ray source can be actuated by pressing an actuation member on mobile unit 600 or by means of a remote control. After exposure is complete, the cassette is inserted into opening 606 of CR scanner 605 for scanning by the CR scanner, whereby a digital image is generated and can be displayed on display 610.

Display 610 can provide options for storing, transmitting, modifying, and printing of the digital medical image.

Mobile unit 600 can be configured whereby exposure cannot be actuated when CR scanner 605 is scanning. Similarly, mobile unit 600 can be configured whereby CR scanner 605 cannot be actuated when x-ray source 640 is exposing. Further, mobile unit 600 can be configured such that there are two electronic systems (one each for the CR scanner and x-ray source) and full isolation between the electronic systems. If the electronic systems are fully isolated, one element (i.e., either the x-ray source or CR scanner) can still be operated should the other element be in need of servicing or repair.

Figure 8:
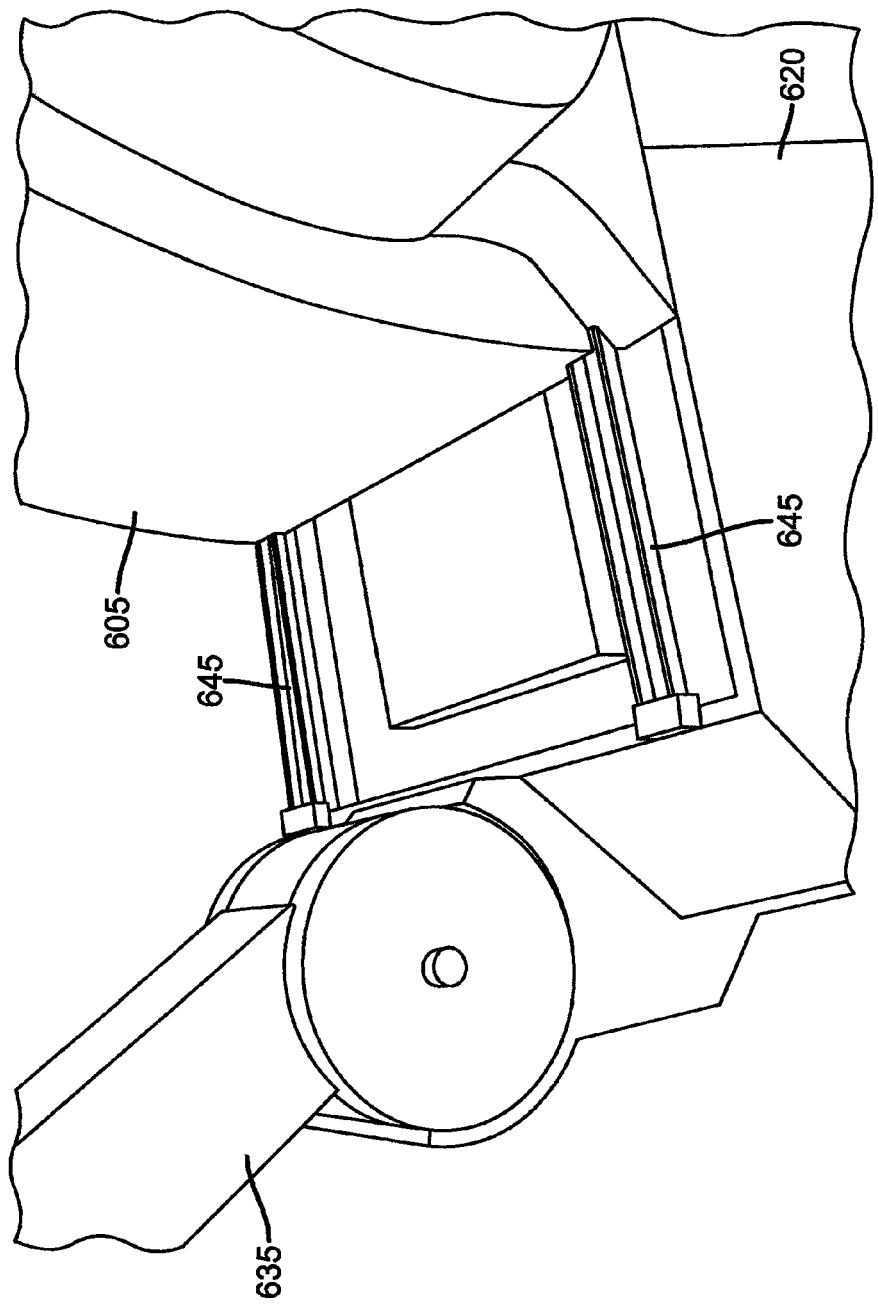
FIGS. 8 and 9 show a perspective view of a portion of the mobile computed radiography unit of FIGS. 6 and 7 wherein the CR scanner is moved in a direction away from the support member to expose the interior of the frame.
Figure 9:
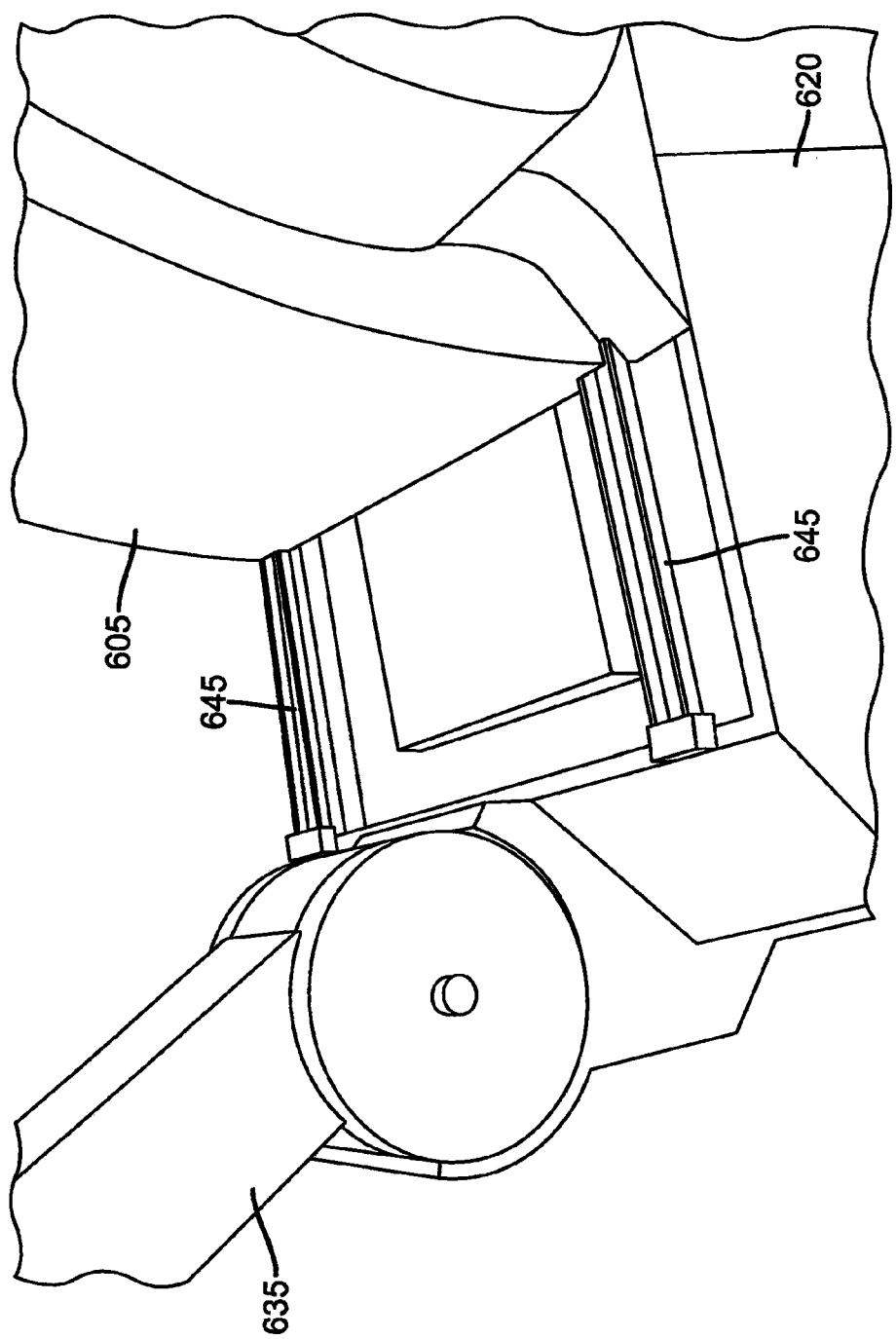

Referring now to FIGS. 8 and 9, for ease of maintenance, CR scanner 625 can be mounted for translational movement relative to frame 620. For example, CR scanner 625 can be mounted to frame 620 using guide rails 645 (or other means known to those skilled in the art for linear movement) to allow CR scanner 625 to move in a planar direction away from support member 635. This would allow access to the interior of frame 620.

In the medical environment, in addition to computed radiography (CR), digital radiography (DR) is also being employed to obtain medical images. For example, see U.S. Pat. No. 7,329,046 (Muszak) titled DIGITAL RADIOGRAPHY IMAGING SYSTEM WITH ROTATABLE DISPLAY AND CONTROLS and U.S. Pat. No. 7,265,355 (Chang) titled METHOD AND SYSTEM FOR ACQUIRING FULL SPINE AND LEG IMAGES USING FLAT PANEL DIGITAL RADIOGRAPHY. Digital detectors are employed with DR applications. For example, see WO 2007/139638 (Jadrich) titled ENCASEMENT FOR DIGITAL RADIOGRAPHY DETECTOR and WO 2007/078684 (Dhurjaty) titled EVENT DETECTION FOR DIGITAL RADIOGRAPHY DETECTOR.

Figure 10:
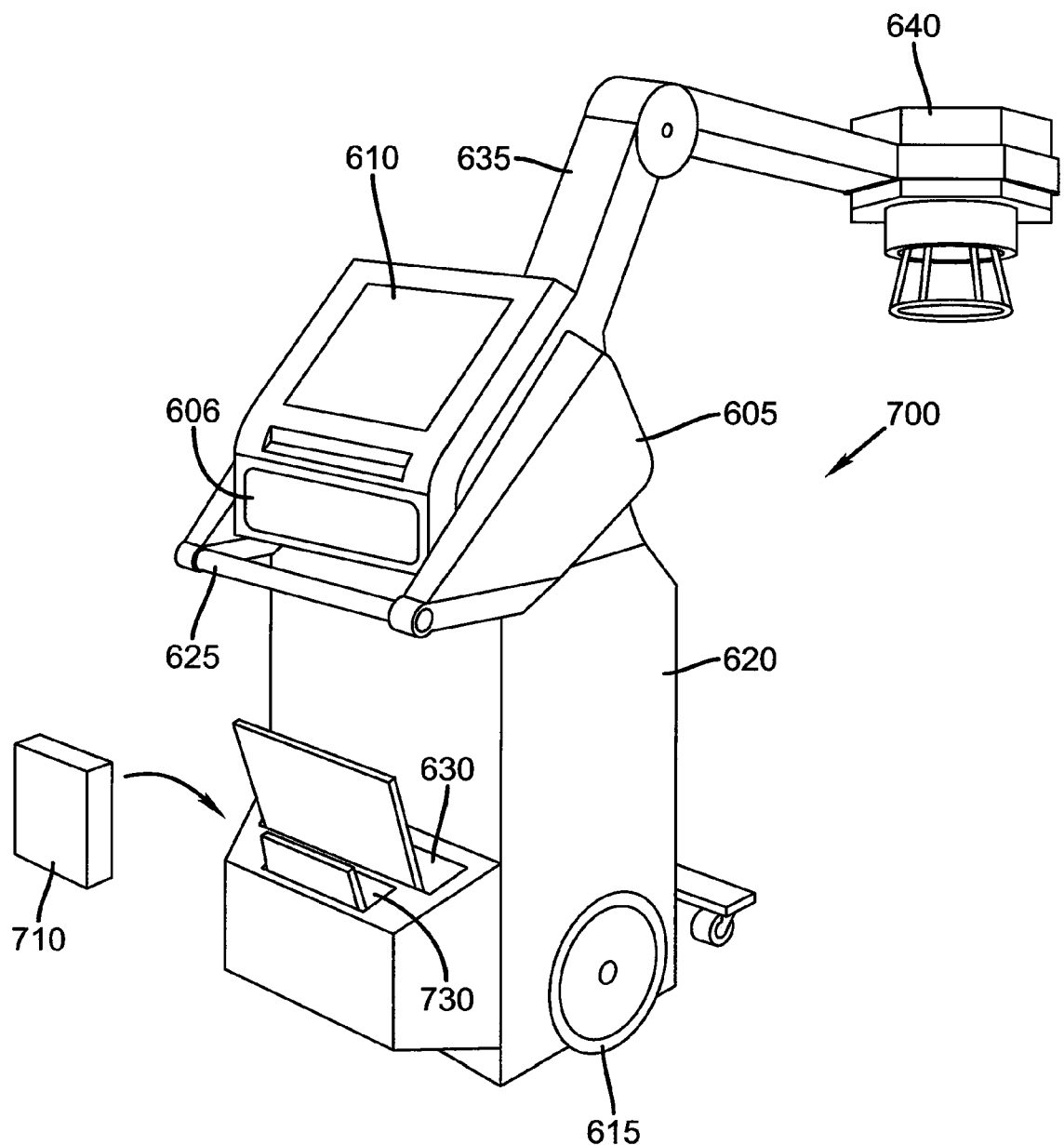
FIG. 10 shows a perspective view of a mobile apparatus comprising computed radiography and digital radiography.

Referring now to FIG. 10, there is shown a mobile apparatus 700 which can be employed for both computed radiography (CR) and digital radiography (DR). As illustrated, CR/DR apparatus 700 includes the features of mobile CR apparatus 600 as described above, and further includes an area/holder 730 for holding/storing one or more digital detectors 710. More particularly, area 730 is a storage area disposed on the frame configured to removably retain at least one digital radiography (DR) detector. The area can be configured to hold one or more detectors and can also be configured to hold one size or multiple sizes detectors.

Figure 11:
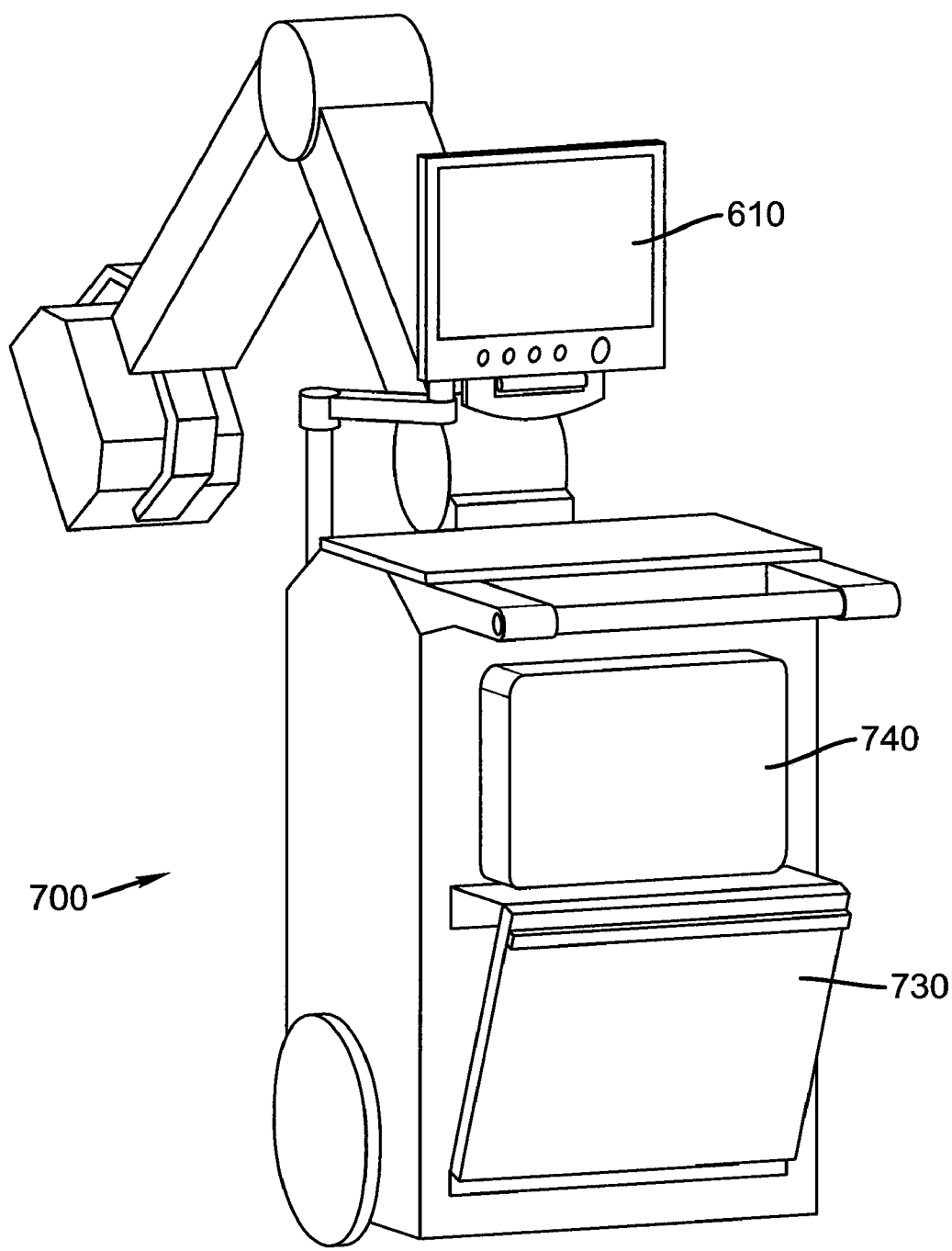
FIG. 11 shows a perspective view of a further mobile apparatus comprising computed radiography and digital radiography.

While FIG. 10 shows DR area 730 adjacent CR holder 630, DR area can be spaced from CR holder 630. For example, referring to FIG. 11, area 730 can be an interior area (such as within the frame). Such a holding area may be desired since detectors 710 can be delicate/fragile units and are typically expensive.

FIG. 11 shows mobile unit 700 including a personal computer (PC) or other controller/processor 740 to control operation of the digital detector. For example, the controller can actuate the digital detector and generator and receive data from the detector. Display 610 is coupled to the frame and connected to the CR scanner and the DR detector to display the one or more images acquired by the CR scanner or DR detector.

When an image is required using mobile apparatus 700, either CR or DR can be employed. If digital detector 710 is employed, digital detector 710, stored in holder 730, is properly positioned relative to the patient. X-ray source 640 is properly positioned for capture of an x-ray image using the digital detector. An appropriate energy level and exposure time for the x-ray source is determined, and this information is communicated to mobile apparatus 700, for example, by means of display 610. Computer 740 can be employed to determine if such information is within generally accepted principles of operation. Exposure by the x-ray source can be actuated by pressing an actuation member on mobile apparatus 700 or by means of a remote control. After exposure is complete, a digital image is generated and can be displayed on display 610. Display 610 can provide options for storing, transmitting, modifying, and printing of the digital medical image.

With mobile apparatus 700, images can be acquired using digital detector 710 while CR scanner 605 is scanning an image acquired using CR, thereby improving the workflow of a medical facility.

It should be appreciated that various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. The invention is capable of other embodiments and of being practiced or of being carried out in various ways. In particular, various aspects of the present invention may be practiced with any construction that facilitates mobile transport of a CR scanner and/or any other components that facilitate mobile image acquisition, viewing, storage or analysis of radiographic images.

In addition, various aspects of the invention described in one embodiment may be used in combination with other embodiments and is not limited by the arrangements and combinations of features specifically described herein. Various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Use of ordinal terms such as "first", "second", "third", and the like, in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A mobile radiography apparatus comprising:
   a frame;
   a transport mechanism coupled to the frame, the transport mechanism adapted to facilitate transport of the mobile apparatus between locations;
   an x-ray source mounted to the frame;
   a computed radiography (CR) scanner coupled to the frame and adapted to acquire one or more images from an image recording medium;
   a storage area disposed on the frame configured to removably retain at least one digital radiography (DR) detector; and
   a display coupled to the frame and connected to the CR scanner and the DR detector to display the one or more images acquired by the CR scanner or DR detector.

2. The mobile apparatus of claim 1, further comprising at least one wireless connection adapted to transmit the one more images wirelessly to at least one storage facility.

3. The mobile apparatus of claim 1, further comprising at least one wireless connection adapted to transmit the one more images wirelessly to at least one storage facility, and the wireless connection is adapted to transmit the one or more images by means of a local area network (LAN) to the at least one storage facility.

4. The mobile apparatus of claim 1, further comprising at least one holder adapted to store at least one CR image recording cassette.

5. The mobile apparatus of claim 1, wherein the x-ray source is mounted to the frame by means of an articulated arm, and the x-ray source is disposed proximate one end of the arm.

6. The mobile apparatus of claim 1, further comprising a power supply, disposed within the frame, adapted to power the x-ray source, the display, and the CR scanner.

* * * * *